(12) United States Patent
Gill et al.

(10) Patent No.: US 8,131,361 B2
(45) Date of Patent: Mar. 6, 2012

(54) SYSTEM AND METHOD FOR SETTING ATRIOVENTRICULAR PACING DELAYS BASED ON FAR-FIELD ATRIAL SIGNALS

(75) Inventors: Jong Gill, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 616 days.

(21) Appl. No.: 12/267,483

(22) Filed: Nov. 7, 2008

(65) Prior Publication Data
US 2010/0121395 A1    May 13, 2010

(51) Int. Cl.
*A61N 1/368* (2006.01)
(52) U.S. Cl. .................................. 607/9; 607/4; 607/27
(58) Field of Classification Search ........................ None
See application file for complete search history.

(56) References Cited

U.S. PATENT DOCUMENTS

| | | | | |
|---|---|---|---|---|
| 5,193,550 | A | * | 3/1993 | Duffin ............................ 600/510 |
| 5,333,615 | A | * | 8/1994 | Craelius et al. ................ 600/509 |
| 6,973,350 | B1 | * | 12/2005 | Levine et al. ................... 607/27 |
| 2009/0299423 | A1 | * | 12/2009 | Min .................................. 607/9 |

* cited by examiner

*Primary Examiner* — Kennedy Schaetzle

(57) ABSTRACT

An intrinsic inter-atrial conduction delay is determined by a pacemaker or implantable cardioverter-defibrillator based, at least in part, on far-field atrial events sensed using ventricular pacing/sensing leads. An atrioventricular pacing delay is then set based on the inter-atrial conduction delay. By detecting atrial events using ventricular leads, rather than using atrial leads, a more useful measurement of the intrinsic inter-atrial conduction delay can be obtained. In this regard, since atrial electrodes detect atrial activity locally around the electrodes, a near-field atrial event sensed using an atrial electrode might not properly represent the actual timing of the atrial event across both the right and left atria. Far-field atrial events sensed using ventricular leads thus allow for a more useful measurement of inter-atrial conduction delays for use in setting atrioventricular pacing delays. The delivery of individual V-pulses to the heart of the patient may be timed relative to the ends of individual far-field atrial events.

20 Claims, 8 Drawing Sheets

EXEMPLARY TECHNIQUE FOR DETERMINING AND USING AV/PV PACING DELAYS

350 — DETERMINE INTER-ATRIAL CONDUCTION DELAYS (PE/AE) USING NEAR-FIELD ATRIAL EVENTS SENSED VIA RIGHT ATRIAL (RA) ELECTRODES AND ALSO USING AMPLIFIED FAR-FIELD ATRIAL EVENTS SENSED VIA VENTRICULAR ELECTRODES:

$$PE = \text{NEAR-FIELD P-WAVE}_{END} - \text{NEAR-FIELD P-WAVE}_{BEG} + \text{TimingDifference(P-wave)}$$
$$AE = \text{NEAR-FIELD AER}_{END} - \text{A-PULSE} + \text{TimingDifference(AER)}$$

WHERE TimingDifference(P-wave) IS THE TIMING DIFFERENCE BETWEEN A FAR-FIELD P-WAVE AND THE CORRESPONDING NEAR-FIELD P-WAVE, AND TimingDifference(AER) IS THE TIMING DIFFERENCE BETWEEN A FAR-FIELD AER AND A CORRESPONDING NEAR-FIELD AER

352 — DETERMINE AV/PV PACING DELAY INTERVALS BASED ON THE MEASURED PE/AE DELAYS, E.G.:

$AV = AE + \delta$; IF $AE < 150$ MS, $\delta = 60$ MS; IF $AE \geq 150$ MS, $\delta = 30$ MS.
$PV = PE + \delta$; IF $PE < 100$ MS, $\delta = 60$ MS; IF $PE \geq 100$ MS, $\delta = 30$ MS.

354 — DELIVER PACING THERAPY USING THE AV/PV PACING DELAY INTERVALS (AND OPTIONAL VV INTERVALS) AND WHILE TIMING THE DELIVERY OF PARTICULAR V-PULSES FOLLOWING THE ENDS OF PRECEDING ATRIAL EVENTS (AS DERIVED FROM THE NEAR-FIELD ATRIAL SIGNALS)

356 — RECORD AV/PV DELAYS FOR DIAGNOSTIC PURPOSES; PERIODICALLY RECALIBRATE AV/PV; OPTIONALLY DETERMINE AV/PV FOR DIFFERENT HEART RATE RANGES

FIG. 6

SYSTEM AND METHOD FOR SETTING ATRIOVENTRICULAR PACING DELAYS BASED ON FAR-FIELD ATRIAL SIGNALS

FIELD OF THE INVENTION

The invention generally relates to implantable cardiac stimulation devices such as pacemakers and implantable cardioverter-defibrillators (ICDs) and, in particular, to techniques for determining and using atrio-ventricular pacing delays for pacing the ventricles of a patient in which such a device is implanted.

BACKGROUND OF THE INVENTION

Clinical studies related to cardiac pacing have shown that an optimal atrioventricular pacing delay (e.g., AV delay or PV delay) can improve cardiac performance. However, such optimal delays depend on a variety of factors that may vary over time. Thus, what is "optimal" can vary over time. An optimization of AV/PV pacing delay may be performed at implantation and sometimes, a re-optimization may be performed during a follow-up consultation. While such optimizations are beneficial, the benefits may not be long-lasting due to changes in various factors related to device and/or cardiac function.

The following patents and patent applications set forth various improved systems and methods for, inter alia, allowing a pacemaker or ICD to determine and/or adjust AV/PV pacing delays (as well as interventricular (VV) pacing delays) so as to help maintain the pacing delays at optimal values: U.S. Pat. No. 7,248,925 to Bruhns et al.; U.S. patent application Ser. No. 10/703,070, filed Nov. 5, 2003, now abandoned; U.S. patent application Ser. No. 10/974,123, filed Oct. 26, 2004 now abandoned; U.S. patent application Ser. No. 10/986,273, filed Nov. 10, 2004 now U.S. Pat. No. 7,590,446; U.S. patent application Ser. No. 10/980,140, filed Nov. 1, 2004 now abandoned; U.S. patent application Ser. No. 11/129,540, filed May 13, 2005 now abandoned; and U.S. patent application Ser. No. 11/952,743, filed Dec. 7, 2007 now abandoned.

In particular, techniques were set forth therein for exploiting inter-atrial conduction delays to set optimal or preferred AV/PV pacing delays to time the delivery of ventricular pacing pulses (V-pulses). It would be desirable to provide additional or alternative techniques for setting AV/PV pacing delays.

In particular, it is desirable to provide improved techniques for detecting the boundaries of atrial events for use in setting the AV/PV delays. In at least some of the patents and patent applications cited above, near-field atrial signals are sensed using electrodes implanted within the atria to detect P-waves (i.e. intrinsic atrial depolarization events) for use in determining the inter-atrial conduction delay of the patient, from which the duration of preferred AV/PV pacing delay intervals are set. Also, some implantable devices trigger the timing of particular AV/PV intervals (for use in delivering particular V-pulses) based on the end of the latest P-wave. However, since atrial electrodes detect atrial activity locally around the electrodes, near-field atrial activity sensed using an atrial electrode might not properly represent the actual timing of atrial events across both the right and left atria. Hence, neither the determination of the preferred duration of the AV/PV pacing delay intervals, nor the triggering of particular AV/PV timing intervals for use in delivering particular V-pulses, is optimal when using near-field atrial activity.

Accordingly, it is desirable to provide systems and methods exploiting far-field atrial signals for use in detecting atrial events for use in setting and using AV/PV pacing delays and it is to this end that aspects of the present invention are directed.

SUMMARY OF THE INVENTION

In accordance with an exemplary embodiment of the invention, techniques are provided for determining and using atrioventricular (AV/PV) pacing delays for use in delivering cardiac pacing therapy to the heart of a patient in which an implantable cardiac stimulation device is implanted, wherein the device is equipped to receive signals from at least one ventricular electrode. Briefly, a far-field atrial event is detected using the ventricular electrode and then an atrioventricular (AV/PV) pacing delay is set for use in pacing the heart of the patient based on the far-field atrial event detected using the ventricular electrode. Preferably, the portion of the ventricular channel signal used for detecting the atrial event is amplified for improved detection.

By detecting atrial events using amplified signals from ventricular electrodes, rather than using signals sensed using atrial electrodes, a more precise and effective detection of the boundaries of atrial events can often be obtained. As noted, since atrial electrodes detect atrial activity locally around the electrodes, a near-field atrial event sensed using an atrial electrode might not properly represent the actual timing of the atrial event across both the right and left atria. For example, the beginning and the end of a near-field P-wave detected using an atrial electrode may not properly represent the actual beginning and end of the P-wave across both the right and left atria. As such, for implantable devices that exclusively use the beginning and end of the P-wave to determine the intra-atrial conduction delay of the patient (for use in setting the duration of atrioventricular pacing delays intervals), the use of the near-field atrial signal may not yield optimal atrioventricular pacing delays intervals. Likewise, for implantable devices that use the end of the P-wave to trigger the timing of particular atrioventricular delay timing intervals (for timing the delivery of particular V-pulses), the exclusive use of the near-field atrial signal may not result in V-pulses being delivered at the optimal times.

By instead exploiting far-field atrial events sensed using ventricular electrodes, a more useful measurement of the boundaries of P-waves is obtained for use in setting the duration of atrioventricular pacing delay intervals and for triggering their activation. The use of far-field atrial signals is also appropriate for use in detecting the boundaries of atrial evoked responses (AERs), i.e. atrial events trigged by A-pulses.

In a first illustrative embodiment, the implantable device identifies the portion of the ventricular channel signal expected to contain the far-field atrial event. The far-field atrial event may be a P-wave or an AER. The ventricular channel may be derived, e.g., using a right ventricular (RV) tip electrode along with the device housing or "can" electrode. However, in some implementations, other electrodes are instead used to derive the ventricular channel, including, e.g., an RV ring electrode, an RV coil electrode, a superior vena cava (SVC) electrode, a left ventricular (LV) tip electrode, an LV ring electrode, an LV coil electrode, as well as one or more pericardial electrodes. The device then determines an isoelectric baseline of the selected portion of the ventricular channel signal and centers the signal on the isoelectric baseline. After the signal is properly centered, the device amplifies the signal by a factor of ten or more to facilitate detection of far-field atrial events therein. Once the far-field events are detected, the device then identifies the beginnings and ends of the events for use in determining the intrinsic intra-atrial conduction delay (A-A) of the patient for use in setting the duration of the AV/PV pacing delay intervals. The device also uses the ends of individual atrial events to time the delivery of V-pulses. That is, the far-field atrial events are used both to set the duration of AV/PV intervals and to time the delivery of particular V-pulses.

In one particular example, intra-atrial delays (AE/PE) are determined as follows:

$$PE = \text{FAR-FIELD } P\text{-WAVE}_{END} - \text{FAR-FIELD } P\text{-WAVE}_{BEG}$$

$$AE = \text{FAR-FIELD } AER_{END} - A\text{-PULSE}$$

where "FAR-FIELD P-WAVE$_{END}$" represents the time of the end of the far-field P-wave sensed on the ventricular channel signal, "FAR-FIELD P-WAVE$_{BEG}$" represents the time of the beginning of the far-field P-wave, "FAR-FIELD AER$_{END}$" represents the time of the end of the far-field AER, and "A-pulse" represents the time of delivery of the A-pulse.

The following equations are then used to set the AV/PV pacing delay intervals based on AE or PE:

$$AV = AE + \delta; \text{ if } AE < 150 \text{ ms}, \delta = 60 \text{ ms}; \text{ if } AE \geq 150 \text{ ms}, \delta = 30 \text{ ms}$$

$$PV = PE + \delta; \text{ if } PE < 100 \text{ ms}, \delta = 60 \text{ ms}; \text{ if } PE \geq 100 \text{ ms}, \delta = 30 \text{ ms}.$$

The AV/PV pacing delays are then used to control pacing therapy. For intrinsic atrial activity, individual V-pulses are delivered following the end of the far-field P-wave, subject to the PV pacing delay. For paced atrial activity, individual V-pulses are delivered following the end of the far-field AER, subject to the AV pacing delay. Note that, once AV/PV delay values have been determined using the aforementioned techniques, the AV/PV delay values can be used to control pacing without necessarily confirming the presence of additional far-field P-waves (or far-field AERs). That is, the device need not continue to detect far-field P-waves (or far-field AERs) while pacing therapy is applied. Preferably, though, the AV/PV delay values are periodically recalibrated by detecting additional far-field P-waves (or far-field AERs). Also, separate AV/PV delay values can be ascertained for different ranges of heart rates by applying the aforementioned techniques at different heart rates.

For biventricular devices, the AV/PV delays are used in conjunction with a VV pacing delay, which may be derived from intrinsic inter-ventricular conduction delays determined based on signals sensed via the ventricular electrodes. Additionally, or alternatively, the AV/PV and VV delays are recorded for diagnostic purposes.

In a second illustrative embodiment, both near-field and far-field atrial events are detected and used to estimate the intra-atrial conduction delays (PE/AE). The near-field atrial events are detecting using one or more atrial electrodes. The far-field atrial events are detecting, as already noted, using one or more ventricular electrodes. The device determines a time delay between the far-field and near-field atrial events to determine the AE/PE delays. The device then sets the AV/PV pacing delays based on the AE/PE delays. In this embodiment, the device also uses the near-field atrial events to time the delivery of V-pulses. For example, V-pulses may be delivered following the end of a near-field intrinsic atrial event (i.e. a P-wave) or following the end of a near-field paced atrial event (i.e. an AER following an A-pulse.)

In one particular example of the second illustrative embodiment, the following equations are used to determine PE and AE:

$$PE = \text{NEAR-FIELD } P\text{-WAVE}_{END} - \text{NEAR-FIELD } P\text{-WAVE}_{BEG} + \text{TimingDifference}(P\text{-wave})$$

$$AE = \text{NEAR-FIELD } AER_{END} - A\text{-PULSE} + \text{TimingDifference}(AER)$$

where TimingDifference(P-wave) is the timing difference between a far-field intrinsic atrial event and the corresponding near-field intrinsic atrial event, and TimingDifference (AER) is the timing difference between a far-field AER and a corresponding near-field AER. Thereafter, the same equations summarized above may be used to set the AV/PV pacing delay intervals based on AE/PE:

$$AV = AE + \delta; \text{ if } AE < 150 \text{ ms}, \delta = 60 \text{ ms}; \text{ if } AE \geq 150 \text{ ms}, \delta = 30 \text{ ms}$$

$$PV = PE + \delta; \text{ if } PE < 100 \text{ ms}, \delta = 60 \text{ ms}; \text{ if } PE \geq 100 \text{ ms}, \delta = 30 \text{ ms}.$$

Various system and method examples of the invention are described in detail herein.

BRIEF DESCRIPTION OF THE DRAWINGS

The above and further features, advantages and benefits of the invention will be apparent upon consideration of the present description taken in conjunction with the accompanying drawings, in which:

FIG. 6 is a flow chart illustrating a second exemplary technique for setting and using AV/PV pacing delays based on far-field atrial events detected using the technique of FIG. 3;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Pacer/ICD System

Figure 1:
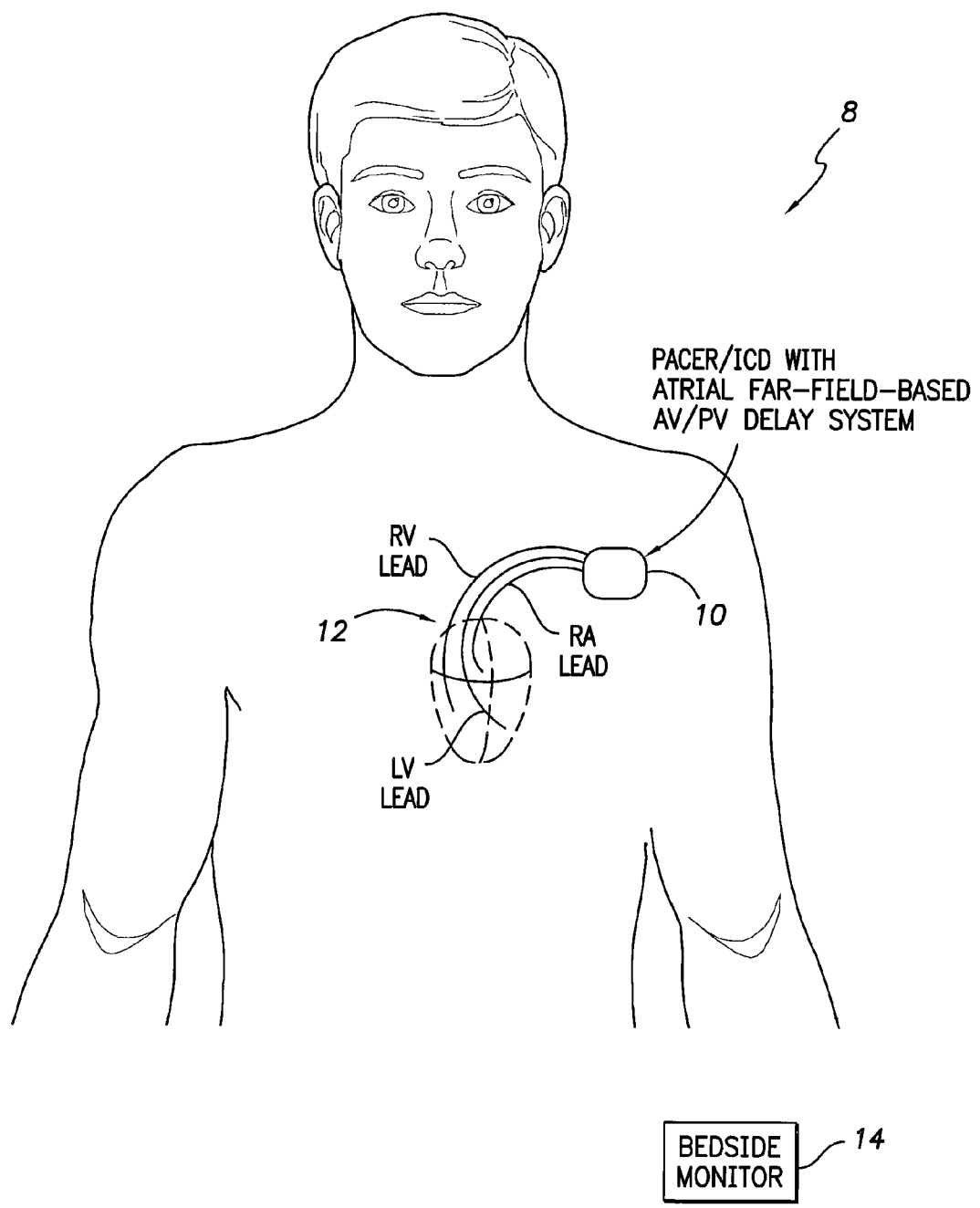
FIG. 1 provides an overview of components of an implantable medical system having a pacemaker or ICD equipped to set AV/PV pacing delay values based on far-field atrial signals sensed using LV or RV leads.

FIG. 1 provides a stylized representation of an implantable medical system 8 capable of delivering pacing therapy and potentially other forms of therapy, such as cardioversion and defibrillation shocks. System 8 includes a pacer/ICD 10 or other cardiac stimulation device that incorporates internal components (shown individually in FIG. 8) for detecting arrhythmias based on electrical cardiac signals sensed via a set of leads 12. In FIG. 1, stylized representations of a right atrial (RA) lead, a right ventricular (RV) lead and a left ventricular (LV) lead are shown. A more precise illustration of the location of the leads and their respective electrodes is provided in FIG. 7.

Briefly, insofar as pacing therapy is concerned, the pacer/ICD is equipped to deliver electrical pacing pulses to the ventricles subject to an atrioventricular pacing delay following atrial activity. That is, following detection of an intrinsic atrial electrical depolarization event (i.e. a P-wave), the pacer/ICD can deliver a ventricular pacing pulse (V-pulse) to the ventricles subject to a PV delay. Following delivery of an atrial pacing pulse (A-pulse), the pacer/ICD can deliver a V-pulse to the ventricles subject to an AV delay.

Whether or not such V-pulses are delivered to the ventricles within a given cardiac cycle depends on the programming of the pacer/ICD and on conditions sensed within the heart of the patient. For example, the pacer/ICD can be set to a demand mode where V-pulses are only delivered if intrinsic ventricular depolarizations (i.e. R-waves or QRS-complexes) are not detected. In other cases, V-pulses may be delivered prior to intrinsic ventricular depolarizations in an effort to improve stroke volume, hemodynamics, or other aspects of cardiac performance. Any of a variety of techniques may be exploited to make determine whether V-pulses are to be delivered, and such techniques will not be described herein. (The use of AV/PV delays for improve hemodynamics is discussed, e.g., in U.S. Pat. No. 6,832,112 to Bornzin, entitled "Method of Adjusting an AV and/or PV Delay to Improve Hemodynamics and Corresponding Implantable Stimulation Device.")

Assuming, though, that V-pulses are to be delivered to a particular patient, the pacer/ICD determines the optimal or preferred pacing delay values for use as the AV and PV delays. To this end, the pacer/ICD preferably employs certain rapid optimization techniques—referred to herein as QuickOpt techniques (where "QuickOpt" is a trademark of St. Jude Medical)—for setting the AV/PV pacing delays based on atrial events. For pacer/ICDs capable of biventricular pacing, the pacer/ICD also preferably determines optimal or preferred VV pacing delay values using QuickOpt for use in separately pacing the left and right ventricles. The QuickOpt rapid optimization techniques are discussed in the patents cited in the Summary section above, which are incorporated by reference herein, particularly insofar as the detailed descriptions of the rapid optimization of AV/PV pacing delays is concerned.

For the purposes of setting the AV/PV pacing delays, the QuickOpt rapid optimization techniques operate to determine the AV/PV delay values based, at least in part, on intra-atrial (A-A) conduction delays within the patient determined based on the width of atrial events (i.e. P-waves and/or AERs).

To determine the intra-atrial conduction delay, pacer/ICD 10 of FIG. 1 is equipped to detect atrial events using the LV or RV leads of FIG. 1, rather than using the RA lead as might otherwise be employed. That is, the pacer/ICD of FIG. 1 detects far-field versions of P-waves and AERs using electrodes of the LV and/or RV leads for the purposes of optimizing the AV/PV pacing delays. Details of the far-field-based AV/PV pacing delay determination techniques used by pacer/ICD 10 are provided below.

In addition to controlling the delivery of pacing therapy based on the AV/PV pacing delays derived from the atrial far-field events, the pacer/ICD also preferably generates and stores diagnostic information pertaining to the AV/PV pacing delays for subsequent clinician review. Such information may be saved within the device for subsequent transmission to a device programmer (not shown in FIG. 1) during a follow-up session between the patient and clinician. Alternatively, if so equipped, the pacer/ICD can transmit the diagnostic data to a bedside monitor 14. Although not shown, the bedside monitor may be directly networked with a centralized computing system, such as the HouseCall™ system of St. Jude Medical, for immediately notifying the physician of any significant changes in patient conditions or through other St. Jude remote follow-up/monitoring such through Merlin@Home and Merlin.net. Networking techniques for use with implantable medical systems are set forth, for example, in U.S. Pat. No. 6,249,705 to Snell, entitled "Distributed Network System for Use with Implantable Medical Devices."

Hence, FIG. 1 provides an overview of an implantable pacer/ICD system capable setting AV/PV pacing delays based on far-field atrial events detected via ventricular leads. Note that systems provided in accordance with the invention need not include all of the components shown in FIG. 1. In many cases, for example, the system will include only the pacer/ICD and its leads, with no bedside monitoring device. Some implementations may employ implantable warning devices or various implantable sensors. These are just a few exemplary embodiments. No attempt is made herein to describe all possible combinations of components that may be provided in accordance with the general principles of the invention. Note also that the particular locations of the implanted components shown in FIG. 1 are merely illustrative and may not necessarily correspond to actual implant locations.

Techniques for Setting AV/VP Delays Based on Far-Field Atrial Events

Figure 2:
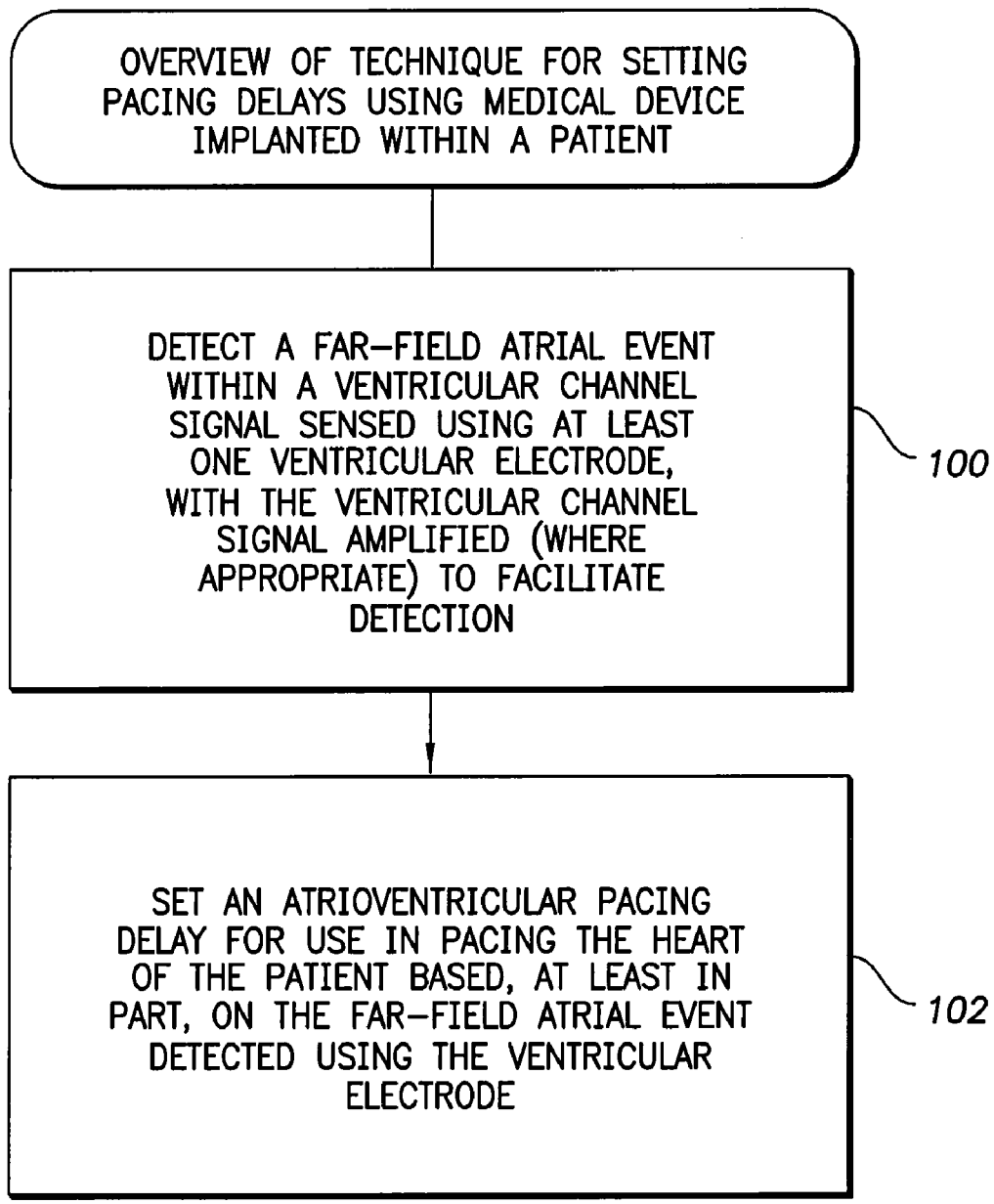
FIG. 2 is a flow chart providing an overview of techniques provided in accordance with the invention for setting AV/PV pacing delays based on far-field atrial signals sensed using LV or RV leads.

FIG. 2 provides an overview of the method performed by the implantable system of FIG. 1. At step 100, the pacer/ICD detects a far-field atrial event within a ventricular channel signal sensed using at least one ventricular electrode, with the ventricular channel signal amplified (where appropriate) to facilitate detection. For example, a unipolar signal derived from an RV electrode may be exploited to detect a far-field P-wave or AER. (In some implementations, other electrodes are instead used to detect the far-field events, such as an RV ring electrode, an RV coil electrode, an SVC electrode, an LV tip electrode, an LV ring electrode, an LV coil electrode, as well as one or more pericardial electrodes, if the device is so equipped.) As will be explained further, pertinent portions of the ventricular channel signal can be amplified, where appropriate, to facilitate detection of the atrial event. That is, within at least some patients, and depending upon the particular ventricular channel being used and other parameters, it may be beneficial to amplify the portion of the ventricular channel expected to contain the far-field atrial event, so as to aid in detection of the event.

At step 102, the pacer/ICD sets at least one atrioventricular pacing delay (such as an AV or PV pacing delay) for use in pacing the heart of the patient in which the device is implanted based on the far-field atrial event detected using the ventricular electrode. Herein, setting an AV/PV delay encompasses, for example, (1) determining the preferred or optimal duration of AV/PV delay intervals for use with a patient and/or (2) triggering particular AV/PV delay timing intervals for use in delivering particular V-pulses. Typically, the preferred or optimal duration of AV/PV delay intervals are determined based on the inter-atrial delay for the patient, which is derived from the beginning and end of atrial far-field events, though other techniques may be used for determining suitable AV/PV delay intervals for a patient based on far-field atrial signals. Likewise, typically, an individual AV/PV delay interval for use in timing the delivery of a particular V-pulse is triggered based on the end of the latest atrial far-field event, though other techniques may be used for activating or triggering particular AV/PV delay intervals based on far-field atrial signals.

Hence, even though the implantable system may include one or more atrial leads, such as the RA lead of FIG. 1, the pacer/ICD nevertheless uses the ventricular leads to detect P-waves and AERs for the purposes of setting and triggering AV/PV pacing delays. As noted, atrial electrodes (such as the electrodes of an RA lead), detect atrial activity locally around the electrodes. The beginning and the end of a near-field P-wave detected using an atrial electrode may not properly represent the actual beginning and end of the P-wave across both the right and left atria. Likewise, the beginning and end a near-field AER detected using an atrial electrode may not properly represent the actual timing of the AER across both the right and left atria. As such, a near-field atrial signal may not allow for a precise determination of the intra-atrial delay of the patient, which is used to set the durations of the AV/PV pacing delays.

By instead using far-field atrial events sensed using ventricular electrodes, a more useful measurement of the boundaries of P-waves and AERs may be obtained for use in determining intrinsic inter-atrial conduction delays within the patient for setting the atrioventricular pacing delays. Also, for devices programmed to time the delivery of V-pulses from the end of P-waves, the end of the far-field P-wave (as detected using a ventricular channel signal) appears to provide a better basis for timing the V-pulses, rather than the end of a near-field P-wave (as detected using an atrial channel signal.)

FIGS. 3-6 illustrate exemplary techniques for setting AV/PV pacing delays, which may be performed in accordance with the general technique of FIG. 2. Beginning at step 200 of FIG. 3, the pacer/ICD senses unipolar signals in the ventricles of the patient using an RV-can sensing channel. At step 202, the pacer/ICD detects R-waves (i.e. QRS-complexes) and T-waves within the unipolar signals. Otherwise conventional ventricular event detection techniques may be employed. At step 204, the pacer/ICD identifies the portions of the unipolar signal expected to include the far-field P-waves or far-field AERs. In general, the next far-field P-wave or AER will likely appear between the end of the latest T-wave and the beginning of the next R-wave. Accordingly, the entire portion of the RV-can signal between the T-wave and the next R-wave can be selected for use in detecting the far-field atrial events. More precise techniques, though, may be exploited for predicting or identifying the particular portion of the ventricular channel signal expected to contain far-field atrial events. See, for example, U.S. Pat. No. 7,349,732 to Kil et al., which describes techniques for identifying far-field atrial signals within the ventricular channel signals.

At step 206, the pacer/ICD then identifies the isoelectric baseline of the selected portion of the ventricular channel signal and re-centers the signals to the baseline (if necessary). At step 208, the pacer/ICD then amplifies at least those portions of the RV-can signal expected to include far-field atrial events, yielding an amplified version of the RV-can signal for use in detecting far-field P-waves or AERs. By amplifying the signal, the far-field atrial events, which may be fairly weak on the ventricular channel, are more easily detected. Also, the far-field events can be ensemble averaged to enhance the signal to noise ratio of the events.

Figure 4:
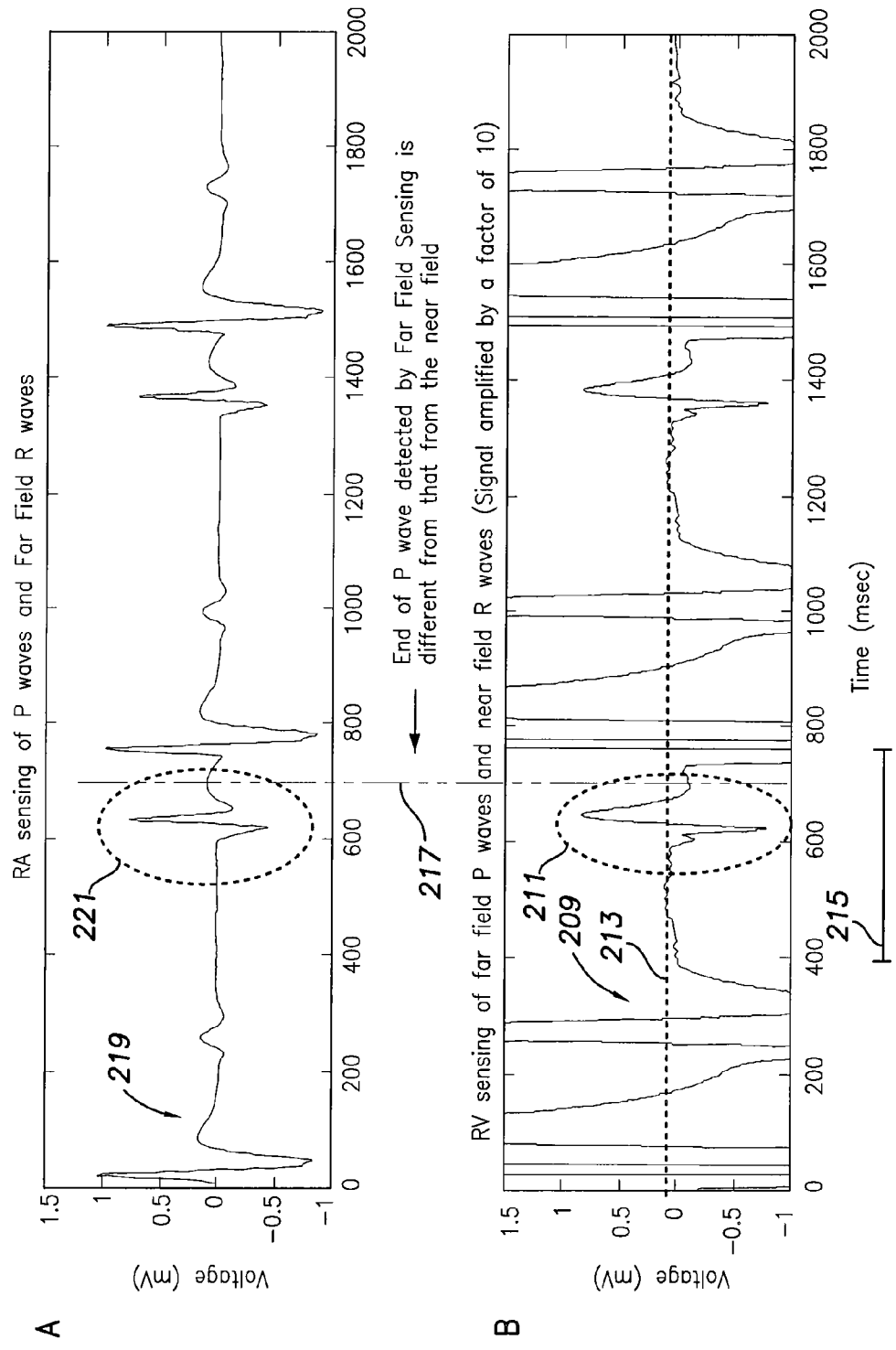
FIG. 4 includes graphs comparing near-field and far-field atrial signals.

FIG. 4 illustrates an amplified RV-can signal 209 including an amplified far-field P-wave 211 (which was amplified relative to an iso-electric baseline 213). In the particular example of FIG. 4, the entire ventricular channel signal is amplified, but only that portion 215 of the RV-can signal between the end of the T-wave and the beginning of the next R-wave is examined to detect the far-field P-wave or AER. In other examples, rather than amplify the entire RV-can signal, only the portion expected to contain the far-field atrial events is amplified (i.e. only segment 215 is amplified). Also, in the example of FIG. 4, the RV-can signal was amplified by a factor of ten. Other amplification factors or gains can instead be used. Otherwise routine experimentation may be used to determine optimal or preferred amplification factors for use with particular sensing channels, leads, or systems and for use with particular patients. Additionally, or alternatively, the sensitivity by which signals are detected can be adjusted on the ventricular channel signal to facilitate detection of far-field P-waves. The detection of an atrial event by a ventricular electrogram (EGM) can also be confirmed by the atrial sensing from the atrial EGM. For instance, if the atrial event detection by far field ventricular EGM is reasonably within (for instance 20 msec) the atrial event detected by atrial EGM, then the far field atrial detection is considered as a true atrial event.

Figure 3:
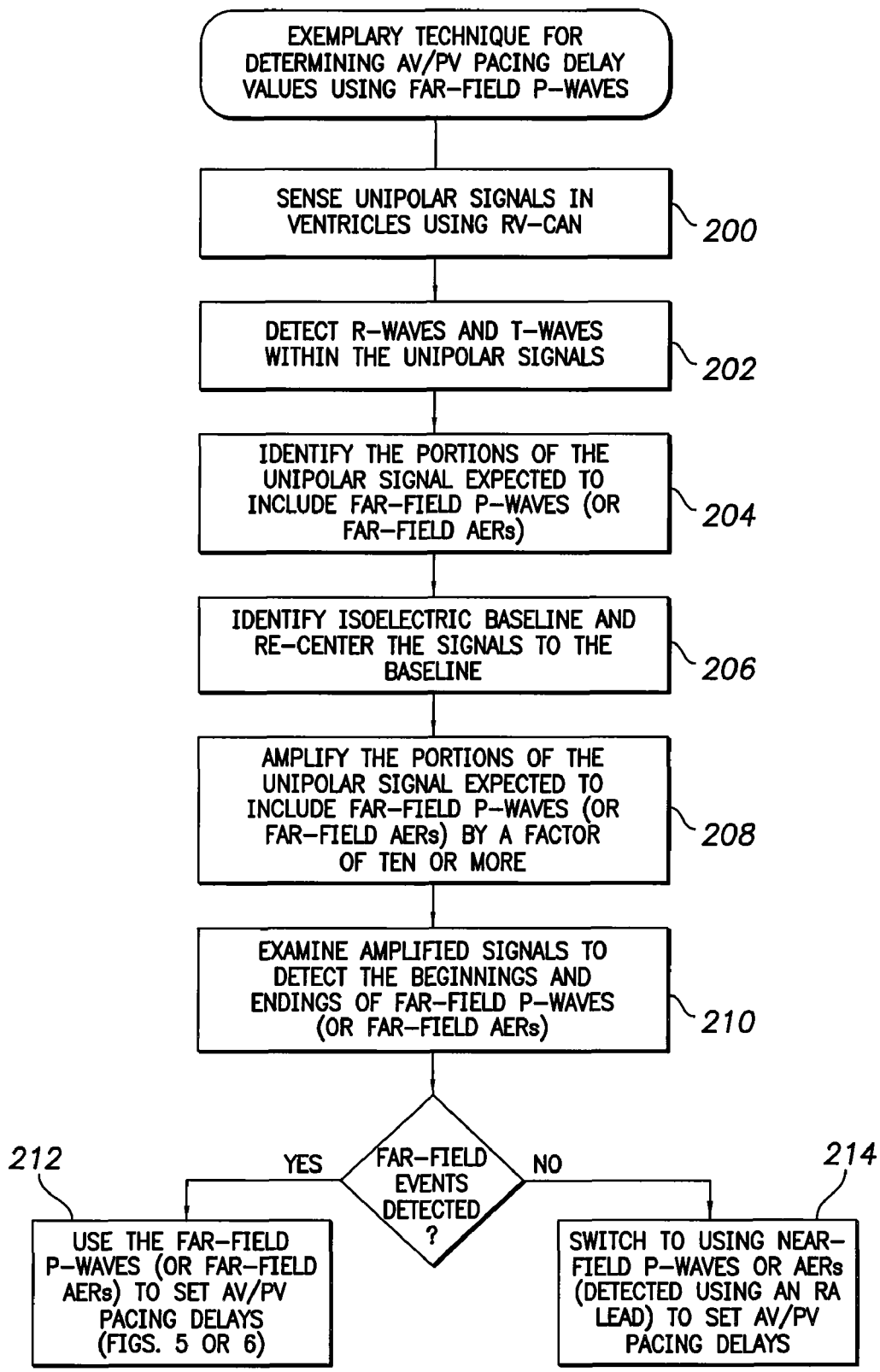
FIG. 3 is a flow chart illustrating an exemplary technique for detecting atrial events based on amplified far-field portions of ventricular channel signals, in accordance with the general technique of FIG. 2.

At step 210 of FIG. 3, the pace/ICD then examines the amplified ventricular channel signals to detect the far-field P-wave (event 211 of FIG. 4) or far-field AERs, particularly the beginning and end of the P-wave (vertical line 217 of FIG. 4), or AER. As explained, in some implementations, the beginning and end of the P-wave and/or AER is used to determine the intra-atrial conduction delay from which the duration of the AV/PV pacing delay is set. Also, in some implementations, the end of the P-wave and/or AER is used to begin tracking the AV/PV delay for use in timing the delivery of the next V-pulse. By detecting the boundaries of the P-wave and/or AER using an amplified far-field signal, rather than a near-field atrial signal, the boundaries of the P-waves and/or AERs are more precisely determined. This is shown in FIG. 4 by way of comparison with an atrial channel RA-can signal 219. The end 217 of the far-field P-wave 211 of the amplified RV-can signal differs from the end of the near-field P-wave 221 of the RA-can signal. Accordingly, for the example of FIG. 4, both the duration of the resulting PV pacing delay interval and the triggering times for activation of individual PV delays will differ.

Returning to FIG. 3, assuming far-field P-waves and/or AERs are properly detected on the RV-can signal, the pacer/ICD, at step 212, uses the far-field atrial events to set the AV/PV delays, as will be explained further with reference to FIG. 5, or using both far-field and near-field atrial events, as will be explained further with reference to FIG. 6. If the pacer/ICD is unable to detect far-field atrial events within ventricular channel signals (perhaps because the far-field atrial events are too weak for the particular patient), the pacer/ICD can then, at step 214, switch to using near-field P-waves and/or AERs detected using an RA lead (or other lead having atrial electrodes) to set the AV/PV delays, assuming at least one lead with atrial electrodes is provided. Note that, prior to switching to the use of near-field atrial events, the pacer/ICD preferably first attempts to detect far-field atrial events by adjusting the amplification of the RV-can signals or by selecting other combinations of ventricular electrodes, such as LV-can, RV coil-can, etc. Near-field atrial signals are preferably only used if the various attempts to detect far-field atrial events are unsuccessful.

Figure 5:
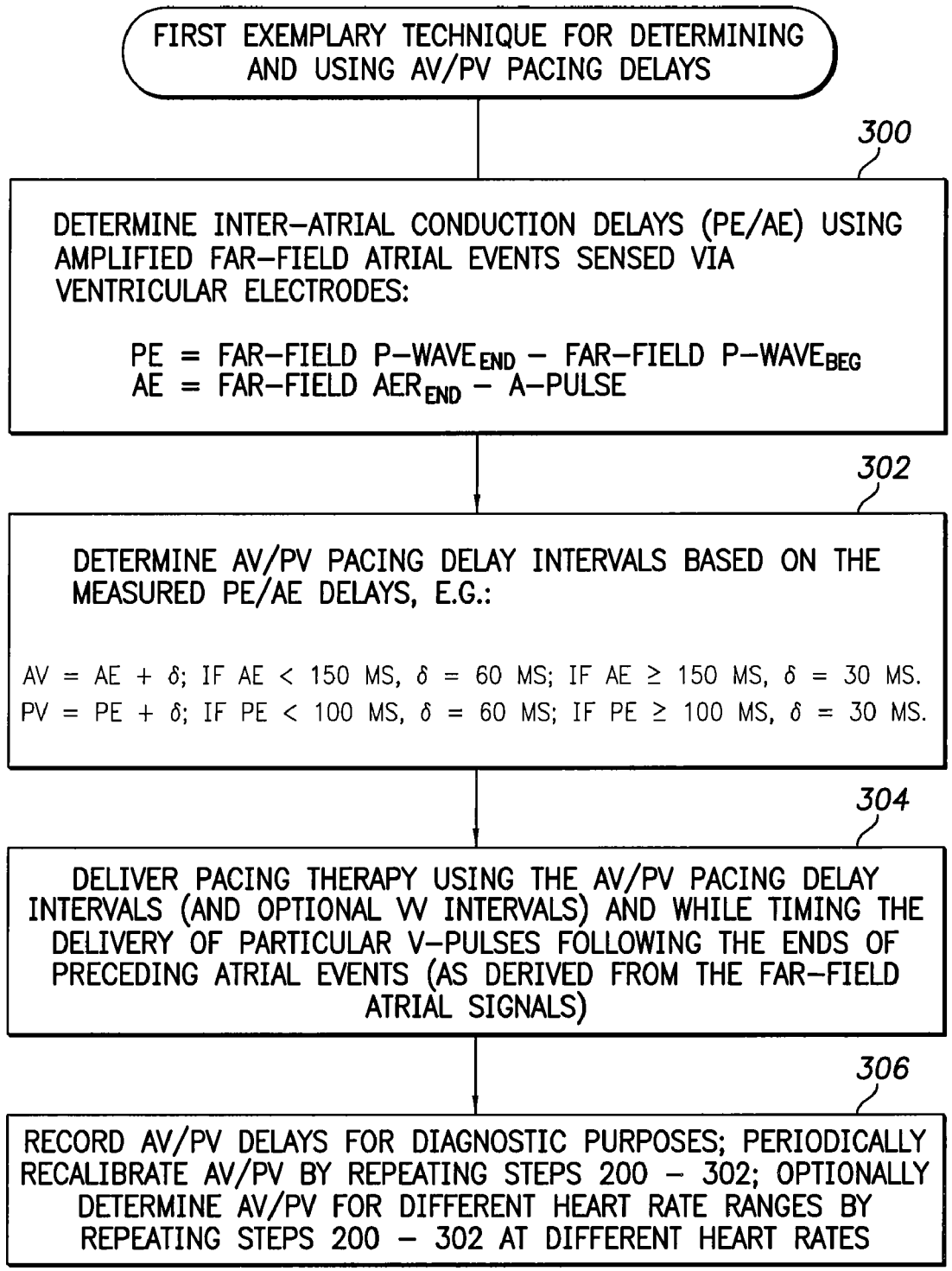
FIG. 5 is a flow chart illustrating a first exemplary technique for setting and using AV/PV pacing delays based on far-field atrial events detected using the technique of FIG. 3.

Turning now to FIG. 5, a first exemplary technique for setting and using AV/PV pacing delays will be described, which exploits the far-field P-waves and/or AERs detected within FIG. 3. At step 300, the pacer/ICD determines inter-atrial conduction delays (PE/AE) for the patient using the amplified far-field atrial events sensed via ventricular electrodes, as in FIG. 3.

In one particular example:

$PE$=FAR-FIELD $P$-WAVE$_{END}$–FAR-FIELD $P$-WAVE$_{BEG}$ $AE$=FAR-FIELD $AER_{END}$–$A$-PULSE where "FAR-FIELD P-WAVE$_{END}$" represents the time of the end of the far-field P-wave sensed on the ventricular channel signal, "FAR-FIELD P-WAVE$_{BEG}$" represents the time of the beginning of the far-field P-wave, "FAR-FIELD AER$_{END}$" represents the time of the end of the far-field AER, and "A-pulse" represents the time of delivery of the A-pulse.

At step 302, the pacer/ICD then determines atrio-ventricular (AV/PV) pacing delay intervals based on the measured inter-atrial (PE/AE) delays, e.g.:

$AV$=$AE$+δ; if AE<150 ms, δ=60 ms; if AE≧150 ms, δ=30 ms.

$PV$=$PE$+δ; if PE<100 ms, δ=60 ms; if PE≧100 ms, δ=30 ms.

More generally, for AV delays, δ is set to a first programmable or hard-coded offset value (T$_1$) if AE is at least equal to a programmable threshold (W$_{AE}$) and is instead set to a second programmable value (T$_2$) if AE is less than W$_{AE}$. In the example shown, T$_1$ is 30 milliseconds (ms), T$_2$ is 60 ms, and W$_{AE}$ is 150 ms. Although these values are typically preferred, other suitable values for T$_1$, T$_2$, and W$_{AE}$ may potentially be used as determined, e.g., via otherwise routine experimentation. Likewise, for PV delays, δ is set to a first programmable value (T$_1$) if PE is at least equal to W$_{PE}$ and is instead set to a second programmable value T$_2$ if PE is less than W$_{PE}$. In the example shown, T$_1$ is again 30 ms and T$_2$ is 60 ms. W$_{PE}$ is 100 ms. Although these values are typically preferred, other suitable values for T$_1$, T$_2$, and W$_{PE}$ may potentially be used as determined, e.g., via otherwise routine experimentation. Also, the T$_1$ and T$_2$ used for calculating AV may differ from those used for calculating PV.

At step 304, the pacer/ICD then delivers pacing therapy to the patient using the AV/PV pacing delay intervals (and optional VV intervals) and while timing the delivery of particular V-pulses following the ends of preceding atrial events (as derived from the far-field atrial signals). Upon detection of the end of a far-field P-wave, the pacer/ICD then begins timing the PV pacing delay interval using a timer and delivers a V-pulse upon expiration of the PV delay interval. Likewise, upon detection of the end of a far-field AER, the pacer/ICD then begins timing the AV pacing delay interval using the timer and delivers a V-pulse upon expiration of the AV delay interval. In some examples, rather than timing the delivery the V-pulses based on the ends of P-waves and/or AERs, the device might instead be programmed to time the delivery based on the beginnings of the atrial events or, in the case of an AER, upon the time of delivery of the A-pulse. If so, then the AV/PV delay intervals may be set somewhat longer by, e.g., providing a larger value for δ. As can be appreciated, a wide range of variations is encompassed herein and the examples provided are merely illustrative.

At step 306, the pacer/ICD records the AV/PV delays for diagnostic purposes. Such information may be stored within device memory for subsequent clinician review.

Note that, once AV/PV delay values have been determined at step 304, the AV/PV delay values can be used to control pacing at step 304 without necessarily confirming the presence of additional far-field P-waves (or far-field AERs). Hence, the device need not continue to detect far-field P-waves (or far-field AERs) while pacing therapy is applied. Preferably, though, the AV/PV delay values are periodically recalibrated by detecting additional far-field P-waves (or far-field AERs). In other words, steps 200-302 are periodically repeated to update the AV/PV delay values. Also, note that separate AV/PV delay values can be ascertained for different ranges of heart rates by applying the aforementioned techniques at different paced or intrinsic heart rates. That is, steps 200-302 can be applied at different heart rates to determine preferred or optimal AV/PV delay values at those heart rates.

Turning now to FIG. 6, a second exemplary technique for setting and using AV/PV pacing delays will be described, which exploits both far-field and near-field P-waves and/or AERs. Some of the steps of FIG. 6 are similar to those of FIG. 5 and only pertinent differences will be described in detail. At step 350, the pacer/ICD determines PE/AE values for the patient using the amplified far-field atrial events sensed via ventricular electrodes, as in FIG. 3, and otherwise conventional near-field atrial events sensed via atrial electrodes, preferably RA electrodes. The near-field RA signals typically need not be amplified.

In one particular example:

$PE$=NEAR-FIELD $P$-WAVE$_{END}$–NEAR-FIELD $P$-WAVE$_{BEG}$+TimingDifference($P$-wave)

$AE$=NEAR-FIELD $AER_{END}$–$A$-PULSE+TimingDifference($AER$)

where TimingDifference(P-wave) is the timing difference between a far-field intrinsic atrial event and the corresponding near-field intrinsic atrial event, and TimingDifference (AER) is the timing difference between a far-field AER and a corresponding near-field AER.

At step 352, the pacer/ICD then determines AV/PV pacing delay intervals based on the PE/AE values using, e.g., the same equations set forth above:

$AV$=$AE$+δ; if AE<150 ms, δ=60 ms; if AE≧150 ms, δ=30 ms.

$PV$=$PE$+δ; if PE<100 ms, δ=60 ms; if PE≧100 ms, δ=30 ms.

At step 354, the pacer/ICD then delivers pacing therapy to the patient using the AV/PV pacing delay intervals (and optional VV intervals) while timing the delivery of particular V-pulses following the ends of preceding atrial events (as derived from the near-field atrial signals). For example, upon detection of the end of a near-field P-wave, the pacer/ICD then begins timing the PV pacing delay interval using a timer and delivers a V-pulse upon expiration of the PV delay interval. Likewise, upon detection of the end of a near-field AER, the pacer/ICD then begins timing the AV pacing delay interval using the timer and delivers a V-pulse upon expiration of the AV delay interval. As discussed above, rather than timing the delivery the V-pulses based on the ends of P-waves and/or AERs, the device might instead time the delivery based on the beginnings of the atrial events or, in the case of an AER, upon the time of delivery of the A-pulse. If so, then the AV/PV delay intervals may be set somewhat longer by, e.g., providing a larger value for δ. As can be appreciated, a wide range of variations is encompassed herein and the examples provided are merely illustrative.

At step 356, the pacer/ICD records the AV/PV pacing delays for diagnostic purposes, periodically recalibrates the AV/PV pacing delays, and/or determines AV/PV pacing delays for different ranges of heart rates by applying the aforementioned techniques at different paced or intrinsic heart rates.

Although described with respect to examples where the determination of the AV/PV delays is performed using the implantable device itself, an external device can alternatively determine the AV/PV delays based on atrial signals sensed by the implantable device, then transmitted to the external device. Still further, although not shown, the pacer/ICD can additionally determine and exploit VV pacing delays for use in biventricular pacing. The patents and patents applications cited above in the background describe various techniques for determining VV pacing delays and for addressing other related issues.

For the sake of completeness, a detailed description of an exemplary implantable cardiac stimulation device will now be described, which may be programmed or otherwise equipped to perform the techniques.

Exemplary Pacer/ICD

Figure 7:
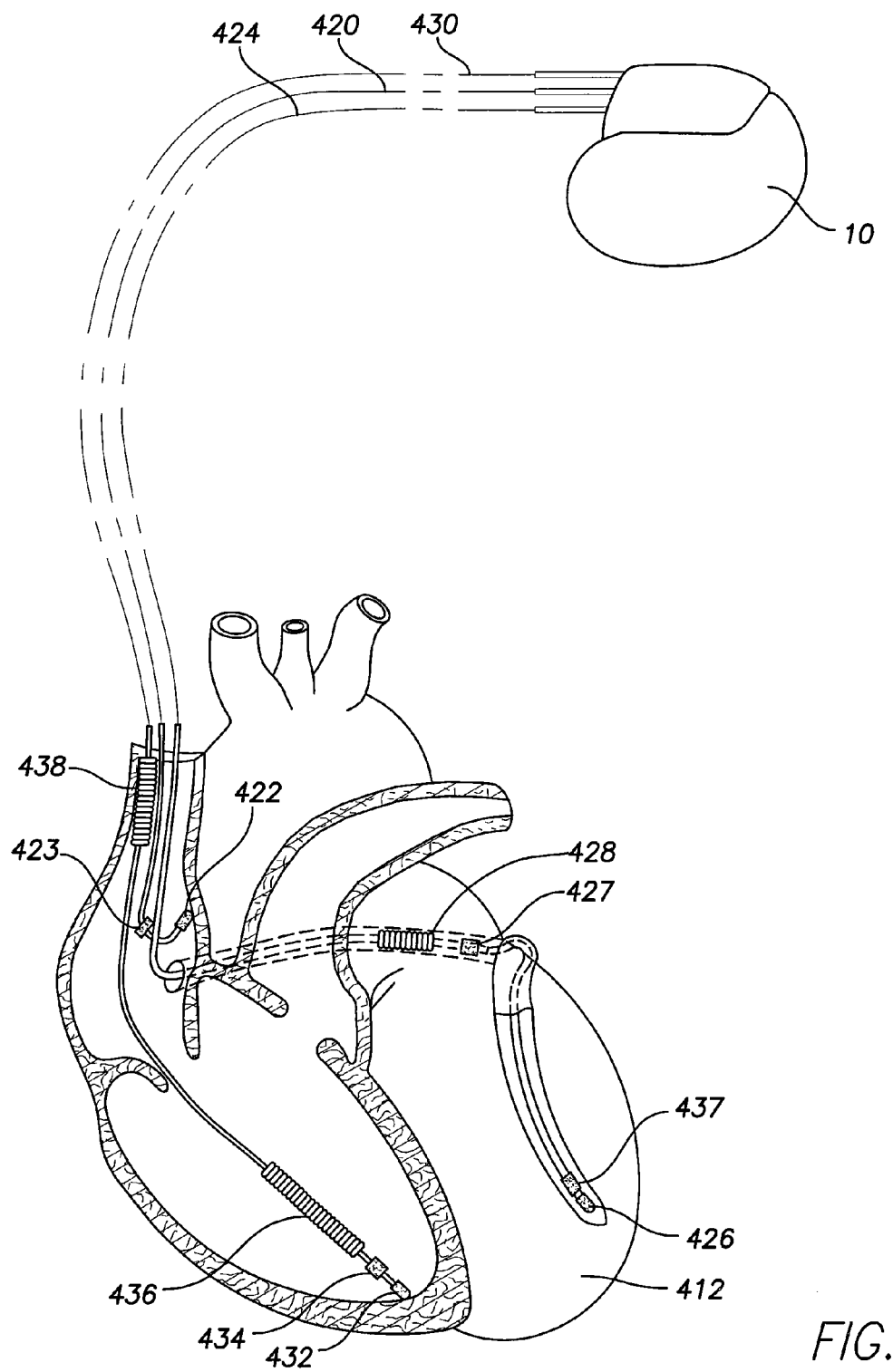
FIG. 7 is a simplified, partly cutaway view, illustrating the pacer/ICD of FIG. 1.
Figure 8:
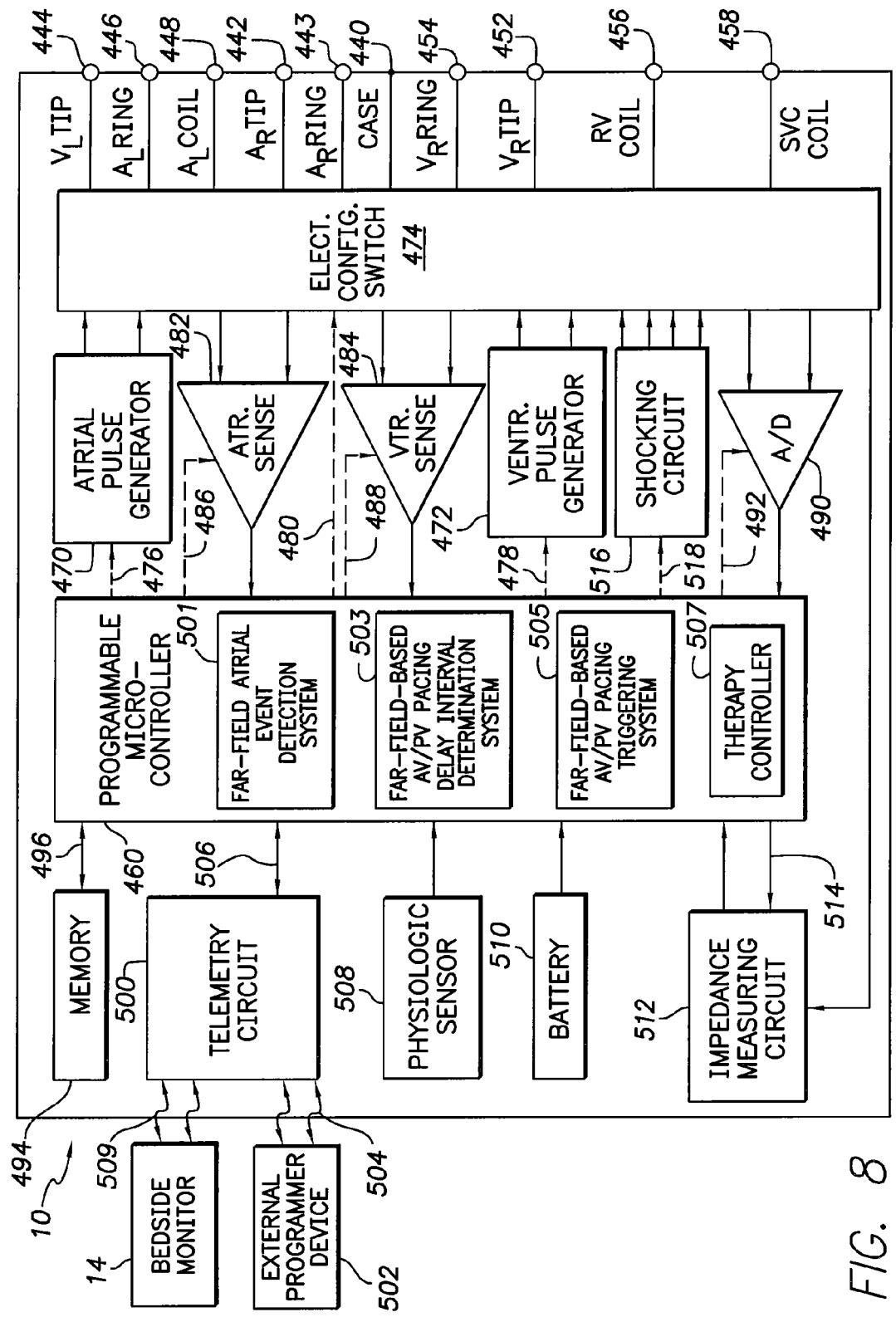
FIG. 8 is a functional block diagram of the pacer/ICD of FIG. 7, illustrating basic circuit elements that provide cardioversion, defibrillation and/or pacing stimulation in the heart and particularly illustrating components for setting AV/PV pacing delays based on far-field atrial signals sensed using LV or RV leads.

With reference to FIGS. 7 and 8, a description of an exemplary pacer/ICD will now be provided. FIG. 7 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle. Although not shown, one or more pericardial leads can be used.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed.

Although only three leads are shown in FIG. 7, it should also be understood that additional stimulation leads (with one or more pacing, sensing and/or shocking electrodes) may be used in order to efficiently and effectively provide pacing stimulation or atrial cardioversion and/or defibrillation.

A simplified block diagram of internal components of pacer/ICD 410 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 440 for pacer/ICD 410, shown schematically in FIG. 8, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423.

To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions is well known in the art.

As shown in FIG. 8, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry used to control the timing of such stimulation pulses (e.g., pacing rate, AV/PV delay, atrial interconduction (interatrial) delay, or V-V delay, etc.) as well as to keep track of the timing of refractory periods, blanking intervals, noise detection windows, evoked response windows, alert intervals, marker channel timing, etc.

Insofar as AV/PV pacing delay values are concerned, the microcontroller includes a far-field atrial event detection system 501 operative to detect far-field atrial events within ventricular channel signals, as described above in connection with FIG. 3. The microprocessor also includes a far-field-based AV/PV pacing delay interval determination system 503 operative to determine suitable AV/PV delay intervals based on the far-field atrial events, as described above in connection with FIG. 5 or based on both near-field and far-field atrial events as described in connection with FIG. 6. The microprocessor also includes a far-field-based AV/PV pacing triggering system 505 operative to trigger the delivery of V-pulses following the ends of far-field P-waves and/or far-field AERs, as also described above in connection with FIG. 5. If pacing pulses are instead to be triggered based on near-field atrial events (as described in connection with FIG. 6), then otherwise conventional pulse timing components of the microcontroller are used. Similar components to those shown within the microcontroller may additionally or alternatively be provided with external programmer device 502 or bedside monitor. Diagnostics information pertaining to AV/PV delays is stored within memory 494. Depending upon the implementation, the various components illustrated within the microcontroller may be implemented as separate hardware or software modules. However, the modules may be combined so as to permit single modules to perform multiple functions.

Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV/PV delay, VV delay, etc.) at which the atrial and ventricular pulse generators, 470 and 472, generate stimulation pulses.

While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 8. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, pacer/ICD 410 is preferably capable of high voltage therapy and appropriate batteries.

As further shown in FIG. 8, pacer/ICD 410 is shown as having an impedance measuring circuit 512, which is enabled by the microcontroller 460 via a control signal 514. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules or more), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules or more), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In general, while the invention has been described with reference to particular embodiments, modifications can be made thereto without departing from the scope of the invention. Note also that the term "including" as used herein is intended to be inclusive, i.e. "including but not limited to."

What is claimed:

1. A method for determining an atrioventricular pacing delay value for use in delivering cardiac pacing therapy to the heart of a patient in which an implantable cardiac stimulation device is implanted, wherein the device is equipped to receive signals from at least one ventricular electrode, the method comprising:
   detecting a far-field atrial event using the ventricular electrode; and
   setting an atrioventricular pacing delay for use in pacing the heart of the patient based on the far-field atrial event detected using the ventricular electrode.

2. The method of claim 1 wherein detecting the far-field atrial event using the ventricular electrode includes:
   sensing an electrical cardiac signal using the ventricular electrode;
   identifying a portion of the electrical cardiac signal expected to include a far-field atrial event; and
   examining the portion of the electrical cardiac signal to detect a far-field event therein.

3. The method of claim 2 wherein examining the portion of the electrical cardiac signal to detect a far-field event therein includes:
   amplifying at least the portion of the electrical cardiac signal expected to include the far-field atrial event; and
   analyzing the amplified portion of the electrical cardiac signal to detect a far-field event therein.

4. The method of claim 2 wherein the portion of the electrical cardiac signal expected to include the far-field atrial event is amplified by a factor of at least ten.

5. The method of claim 2 wherein, prior to amplifying the portion of the electrical cardiac signal, the device performs the steps of:
   identifying an isoelectric baseline of the electrical cardiac signal; and
   centering the electrical cardiac signal on the isoelectric baseline.

6. The method of claim 1 wherein detecting a far-field atrial event using the ventricular electrode is performed to detect both the beginning and the end of the far-field atrial event.

7. The method of claim 6 wherein setting an atrioventricular pacing delay based on the far-field atrial event includes:
   determining an intra-atrial conduction delay for the patient based on the beginning and the end of the far-field atrial event; and
   determining the duration of an atrioventricular pacing delay interval based on the intra-atrial conduction delay.

8. The method of claim 1 wherein detecting a far-field atrial event using the ventricular electrode is performed to detect at least the end of a far-field atrial event.

9. The method of claim 8 wherein setting an atrioventricular pacing delay based on the far-field atrial event includes:
   triggering the timing of a particular atrioventricular pacing delay interval for a particular cardiac cycle based on the end of the far-field atrial event; and delivering a ventricular pacing pulse upon completion of the particular atrioventricular pacing delay interval.

10. The method of claim 1 further including detecting a near-field atrial event using an atrial electrode and wherein setting an atrioventricular pacing delay based on the far-field atrial event includes:
   determining a time delay between the far-field atrial event and the near-field atrial event;
   determining the duration of an atrioventricular pacing delay interval based on the time delay.

11. The method of claim 1 wherein detecting the far-field atrial event using the ventricular electrode is performed using one or more of a right ventricular (RV) tip electrode, an RV ring electrode, an RV coil electrode, a superior vena cava (SVC) electrode, a left ventricular (LV) tip electrode, an LV ring electrode, and an LV coil electrode in combination with a device housing electrode.

12. The method of claim 1 wherein, if the device is unable to detect a far-field atrial event using the ventricular electrode, then a near-field atrial event is instead detected using at least one atrial electrode.

13. The method of claim 12 wherein detecting the near-field atrial event using the atrial electrode is performed using a right atrial (RA) electrode in combination with a device housing electrode.

14. The method of claim 1 wherein the atrial event is representative of an intrinsic atrial depolarization (P-wave).

15. The method of claim 1 wherein the atrial event is representative of an atrial evoked response (AER).

16. The method of claim 15 for use with a device equipped to deliver biventricular pacing therapy and further comprising:
   determining an inter-ventricular (VV) pacing delay value; and
   delivering biventricular pacing therapy based on the atrioventricular pacing delay and the inter-ventricular pacing delay value.

17. The method of claim 1 further comprising delivering pacing therapy using the implantable cardiac stimulation device subject to the atrioventricular pacing delay.

18. The method of claim 1 wherein the steps of detecting far-field atrial events using the ventricular electrode and setting the atrioventricular pacing delay based on far-field atrial events are repeated at different heart rates to obtain atrioventricular pacing delay values for different heart rate ranges.

19. A system for use in determining an atrioventricular pacing delay value for delivering cardiac pacing therapy to the heart of a patient in which an implantable cardiac stimulation device is implanted, wherein the device is equipped to receive signals from at least one ventricular electrode, the system comprises:
   a far-field atrial event detection system operative to detect far-field atrial events using the ventricular electrode; and
   a far-field-based atrioventricular pacing delay value system operative to set an atrioventricular pacing delay value based on far-field atrial events detected using the far-field atrial event detection system.

20. A system for use in determining an atrioventricular delay value for delivering cardiac pacing therapy to the heart of a patient in which an implantable cardiac stimulation device is implanted, wherein the device is equipped to receive signals from at least one ventricular electrode, the system comprises:
   means for detecting a far-field atrial event using the ventricular electrode; and
   means for setting an atrioventricular pacing delay for use in pacing the heart of the patient based on the far-field atrial event detected using the ventricular electrode.

* * * * *